United States Patent
Van Der Louw et al.

(10) Patent No.: US 6,949,531 B2
(45) Date of Patent: Sep. 27, 2005

(54) 14 β, 16, 17-METHYLENE STEROIDS AS NOVEL ANDROGENS

(75) Inventors: Jaap Van Der Louw, Bh Oss (NL); Dirk Leysen, Bh Oss (NL); Marcel Evert De Gooijer, Dutch (NL)

(73) Assignee: Akzo Nobel N.V., Arnhem (NL)

( * ) Notice: Subject to any disclaimer, the term of this patent is extended or adjusted under 35 U.S.C. 154(b) by 231 days.

(21) Appl. No.: 10/450,278

(22) PCT Filed: Dec. 5, 2001

(86) PCT No.: PCT/EP01/14481

§ 371 (c)(1),
(2), (4) Date: Jun. 11, 2003

(87) PCT Pub. No.: WO02/48171

PCT Pub. Date: Jun. 20, 2002

(65) Prior Publication Data

US 2004/0030165 A1 Feb. 12, 2004

(30) Foreign Application Priority Data

Dec. 11, 2000 (EP) .......... 00204459

(51) Int. Cl.$^7$ .......... A61K 31/56; C07J 53/00
(52) U.S. Cl. .......... 514/169; 514/177; 514/182; 552/514
(58) Field of Search .......... 552/514; 514/169, 514/177, 182

(56) References Cited

U.S. PATENT DOCUMENTS 3,732,209 A  5/1973  Fahrenholtz et al.

FOREIGN PATENT DOCUMENTS

WO  00 53619 A  9/2000

*Primary Examiner*—Barbara P. Badio
(74) *Attorney, Agent, or Firm*—William M. Blackstone; Mark W. Milstead

(57) ABSTRACT

Disclosed are androgenic steroids of the (14β,17α)-17-(hydroxymethyl) type. The invention relates to an improvement thereof, which is based on the presence of a β-oriented, annellated cyclopropyl group which includes carbon atoms 16 and 17 of the steroid skeleton, i.e. a 16,17β-methylene moiety. These steroids show an unexpectedly high androgenic potency.

13 Claims, No Drawings

14 β, 16, 17-METHYLENE STEROIDS AS NOVEL ANDROGENS

This application is a 371 of PCT/EP01/14481 filed Dec. 5, 2001.

The invention is in the field of (14β,17α)-17-(hydroxymethyl) steroids which are potent androgens. 0.5

Androgenic steroids having a 14β, 17α-configuration with the 17α-moiety being a hydroxymethyl group are known from WO 00/53619 (with the OH of the hydroxymethyl group being substituted or not). The androgens described therein are generally very potent, and highly suitable for therapeutic use. Nevertheless it is always desired, almost by definition, to provide alternative steroids having similarly high or, preferably, higher potency. Unexpectedly, the present inventors hit upon steroids that are structurally related to a selected group of compounds within WO 00/53619, having a suprisingly high potency.

The invention resides in compounds of the type mentioned in the opening paragraph, which are characterized by having a β-oriented, annellated cyclopropyl group which includes carbon atoms 16 and 17 of the steroid skeleton. The term "hydroxy" should be read so as to include substituted hydroxyl groups.

For completeness' sake it is noted that, incidentally, 16,17-methylene (i.e. annellated cyclopropyl) steroids are known. The cyclopropyl rings therein are α-oriented, and the disclosures do not have any bearing on androgens. Background art of this type includes D. Burn et al., J. Chem. Soc. (1963), 4242–4248, BE 718660, BE 727577, EP 411733, and DD 289542.

More particularly, the invention relates to compounds satisfying the general formula I given below:

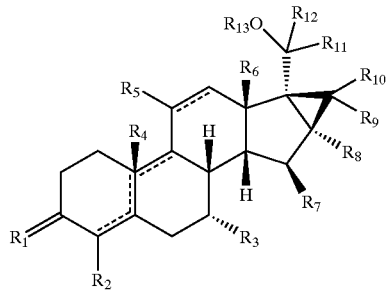

Formula I wherein $R_1$ is O, (H,H), (H,OR), NOR, with R being hydrogen, ($C_{1-6}$) alkyl, ($C_{1-6}$) acyl; O or (H,βOH) is preferred;
$R_2$ is hydrogen, or ($C_{1-6}$) alkyl;
$R_3$ is hydrogen; or $R_3$ is ($C_{1-6}$) alkyl, ($C_{2-6}$) alkenyl, or ($C_{2-6}$) alkynyl, optionally substituted by halogen; hydrogen or methyl is preferred;
$R_4$ is hydrogen, or ($C_{1-6}$) alkyl;
$R_5$ is hydrogen, ($C_{1-6}$) alkyl, or ($C_{2-6}$) alkenyl;
$R_6$ is ($C_{1-6}$) alkyl;
$R_7$ is hydrogen, ($C_{1-6}$) alkyl, ($C_{2-6}$) alkenyl, or (Cl $_6$) alkoxy;
$R_8$ is hydrogen, or ($C_{1-6}$) alkyl;
$R_9$ and $R_{10}$ are independently hydrogen, ($C_{1-4}$) alkoxy, halogen, ($C_{1-4}$) alkyl, or ($C_{2-4}$) alkenyl;
$R_{11}$ and $R_{12}$ are independently hydrogen, ($C_{1-6}$) alkyl, ($C_{2-6}$) alkenyl, ($C_{3-6}$) cycloalkyl, ($C_{5-6}$) cycloalkenyl, or ($C_{2-6}$) alkynyl, each optionally substituted by (Cow) alkoxy, or halogen;
$R_{13}$ is hydrogen, $SO_3H$, or ($C_{1-15}$) acyl; hydrogen or acyl is preferred and the dotted lines indicate optional bonds, whereby a $\Delta^{4(5)}$ double bond is preferred.

Preferred compounds are those according to the above formula I wherein $R_1$ is O (oxo) or (H,OH), notably (3α-H,3β-hydroxy); $R_4$ is hydrogen; $R_6$ is methyl, and wherein the doffed lines indicate a $\Delta^4$ double bond (i.e. a double bond between carbon atoms 4 and 5 of the steroid skeleton), with further preferred compounds being those wherein $R_3$ is hydrogen or methyl. A specifically preferred compound is (7α,14β,16α,17α)-16,17-dihydro-17-(hydroxymethyl)-7-methyl-3'H-cyclopropa[16,17]estra-4,16-dien-3-one, of which the 3β-OH analog is an effective prodrug.

In general, a preferred steroid for carrying out the invention has formula I wherein $R_4$ is hydrogen, $R_6$ is methyl and does not have a $\Delta^{5(10)}$ nor a $\Delta^{11(12)}$ double bond. Furthermore, those compounds are more preferred having those meanings of $R_4$ and $R_6$ and wherein $R_1$ is O, (H,H), (H,OH); $R_2$ is hydrogen, or methyl; $R_3$ is hydrogen, methyl, ethyl or vinyl; $R_5$ is hydrogen or methyl; $R_7$ is hydrogen; RB is hydrogen; $R_9$ is hydrogen, ($C_{1-4}$) alkoxy, halogen, ($C_{1-4}$) alkyl, or ($C_{2-6}$) alkenyl; $R_{10}$ is hydrogen and $R_{11}$ and $R_{12}$ are independently hydrogen, ($C_{1-6}$) alkyl, ($C_{2-6}$) alkenyl, ($C_{3-6}$) cycloalkyl, ($C_{5-6}$) cycloalkenyl, or ($C_{2-6}$) alkynyl, each optionally substituted by ($C_{1-4}$) alkoxy, or halogen. Particularly preferred out of these compounds is a steroid wherein one of $R_{11}$ and $R_{12}$ is hydrogen and the other is hydrogen or 20S methyl, 20S ethyl or 20S ethynyl. Out of this selection particularly good results are obtained with a steroid wherein $R_2$ is hydrogen; $R_5$ is hydrogen; P, is hydrogen; $R_{11}$ and $R_{12}$ are (H,20S methyl) and the steroid does not have a $\Delta^{9(10)}$ double bond.

The term ($C_{1-6}$) alkyl as used in the definition of formula I means a branched or unbranched alkyl group having 1–6 carbon atoms, like methyl, ethyl, propyl, isopropyl, butyl, isobutyl, tertiary butyl, pentyl, and hexyl. Likewise, the term ($C_{1-4}$) alkyl means an alkyl group having 1–4 carbon atoms. Preferred alkyl groups have 1–4 carbon atoms, and most preferred alkyl groups are methyl and ethyl.

The term ($C_{2-6}$) alkenyl means a branched or unbranched alkenyl group having at least one double bond and 2–6-carbon atoms. Likewise, the term ($C_{2-4}$) alkenyl means an alkenyl group having 2–4 carbon atoms. Preferred alkenyl groups have 2 or 3 carbon atoms, such as vinyl and propenyl.

The term ($C_{2-6}$) alkynyl means a branched or unbranched alkynyl group having at least one triple bond and 2–6 carbon atoms. Preferred alkynyl groups have 2–4 carbon atoms, such as ethynyl and propynyl.

The term ($C_{3-6}$) cycloalkyl means a cycloalkane ring having 3–6 carbon atoms, like cyclopropane, cyclobutane, cyclopentane and cyclohexane.

The term ($C_{5-6}$) cycloalkenyl means a cycloalkene ring having at least one double bond and 5 or 6 carbon atoms.

The term ($C_{1-6}$) alkoxy means a branched or unbranched alkyloxy group having 1–6 carbon atoms, like methyloxy, ethyloxy, propyloxy, isopropyloxy, butyloxy, isobutyloxy, tertiary butyloxy, pentyloxy, and hexyloxy. Likewise, the term ($C_{1-4}$) alkoxy means a branched or unbranched alkyloxy group having 1–4 carbon atoms. Preferred alkyloxy groups have 1–4 carbon atoms, and most preferred is methyloxy.

The term ($C_{1-6}$) acyl means an acyl group derived from a carboxylic acid having 1–6 carbon atoms, like formyl, acetyl, propanoyl, butyryl, 2-methylpropanoyl, pentanoyl, pivaloyl, and hexanoyl. Likewise, the term ($C_{1-15}$) acyl means an acyl group derived from a carboxylic acid having 1–15 carbon atoms. Also included within the definition of ($C_{1-6}$) acyl or ($C_{1-15}$) acyl are acyl groups derived from dicarboxylic acids, like hemi-maloyl, hemi-succinoyl, hemi-glutaroyl, and so on.

The term halogen means fluorine, chlorine, bromine, or iodine. When halogen is a substituent at an alkyl group, like in the definition $R_3$, $R_9$, $R_{10}$, $R_{11}$ and $R_{12}$, Cl and F are preferred, F being most preferred.

It is understood that the (14β,17α)-17-(hydroxymethyl) steroids of the invention have the natural configurations 5α, 8β, 9α, 10β, 13β.

The (14β,17α)-17-(hydroxymethyl) steroids of this invention have the natural configurations 5α, 8β, 9α, 10β, 13β, and possess also one or more additional chiral carbon atoms. The compounds may therefore be obtained as a pure diastereomer, or as a mixture of diastereomers. Methods for obtaining the pure diastereomers are well known in the art, e.g. crystallization or chromatography.

For therapeutic use, salts of the compounds of formula I [e.g. salts of compounds wherein $R_{13}$ is $SO_3H$] are those wherein the counterion is pharmaceutically acceptable. However, salts of the acids according to formula I may also find use, for example, in the preparation or purification of a pharmaceutically acceptable compound. All salts, whether pharmaceutically acceptable or not, are included within the ambit of the present invention. Examples of salts of acids according to the invention are mineral salts such as sodium salt, potassium salt, and salts derived from organic bases like ammonia, imidazole, ethylenediamine, triethylamine and the like.

The compounds of the invention as described hereinbefore in general possess an unexpected androgenic activity. Androgenic activity can be measured in various ways. Thus, the potency of androgens can be determined in vitro using the cytoplasmic androgen receptor from human breast tumor cells (MCF-7 cell line); see Berglink, E. W. et al, *Comparison of the receptor binding properties of nandrolone and testosterone under in vitro and in vivo conditions*, J. Steroid Biochem. 22, 831–836 (1985). It is also possible to use Chinese hamster ovary (CHO) cells transfected with the human androgen receptor (incubation time 16 h, temperature 4° C.) and compared with the affinity of 5α-dihydrotestosterone [according to the procedure described by Berglink, E. W. et al, J. Steroid Biochem. 19, 1563–1570 (1983)]. The transactivative androgen activity of the compounds of the invention can be measured, e.g. in Chinese hamster ovary cells (CHO) transfected with the human androgen receptor (hAR), in combination with a mouse mammary tumor virus (MMTV), and luciferase receptor gene (incubation time 16 h, temperature 37° C.) and compared with the activity of St-dihydrotestosterone [according to the procedure described by Schoonen, W. G. E. J. et al, Analyt. Biochem. 261, 222–224 (1998)]. For the in vivo potency determination of androgens the classical Hershberger test can be used. In this test the androgenic (increase in prostate weight) and anabolic activities [increase of the musculus levator ani (MLA)] of a compound are tested in immature castrated rats after daily administration for 7 days; see Hershberger, L. G. et al, *Myotrophic activity of 19-Nortestosteronie and other steroids determined by modified levator ani muscle method*, Proceedings of the society for experimental biology and medicine 83, 175–180 (1953). Additionally, the effect of an androgenic compound on LH suppression can be tested in mature castrated rats according to Kumar, N. et al, *The biological activity of 7alpha-methyl-19-nortestosterone is not amplified in male reproductive tract as is that of testosterone*, Endocrinology 130, 3677–3683 (1992).

As androgenic hormones the (14β,17α)-17-(hydroxymethyl) steroids of the present invention can be used in, int.al., male contraception and male HRT (hormone replacement therapy). Thus, e.g. male contraception may comprise a regimen of administration of hormones in which a progestagen serves to achieve a contraceptive effect and an androgen serves to supplement the resulting decreased testosterone level. Another option is that male contraception is performed with an androgenic hormone alone. The androgens can also be used for androgen supplementation in the partially androgen deficient ageing male. Next to the use in the male, the androgens of the invention also can be used in the female, e.g. as androgen replacement therapy in post-menopausal women.

The present invention also relates to a pharmaceutical composition comprising a steroid compound according to the invention mixed with a pharmaceutically acceptable auxiliary, such as described in the standard reference, Gennaro et al, *Remmington's Pharmaceutical Sciences*, (18th ed., Mack Publishing Company, 1990, see especially Part 8: Pharmaceutical Preparations and Their Manufacture). The mixture of the steroid compounds according to the invention and the pharmaceutically acceptable auxiliary may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. nasal spray. For making dosage units, e.g. tablets, the use of conventional additives such as fillers, colorants, polymeric binders and the like is contemplated. In general any pharmaceutically acceptable additive which does not interfere with the function of the active compounds can be used. The steroid compounds of the invention may also be included in an implant, a vaginal ring, a patch, a gel, and any other preparation for sustained release.

Suitable carriers with which the compositions can be administered include lactose, starch, cellulose derivatives and the like, or mixtures thereof used in suitable amounts.

Furthermore, the invention relates to the use of the steroid compound according to the invention for the manufacture of a medicament in the treatment of androgen-deficiency, such as in male or female HRT (hormone replacement therapy). Accordingly, the invention also includes a method of treatment in the field of male or female HRT, comprising the administration to a male or female patient suffering from an androgen-deficiency, of a compound as described hereinbefore (in a suitable pharmaceutical dosage form).

Further, the invention relates to the use of a steroid compound according to the invention for the manufacture of a medicament having contraceptive activity (for which in the art the term "contraceptive agent" is also used). Thus the invention also pertains to the medical indication of contraception, i.e. a method of contraception comprising the administration to a subject, being a male, preferably a human male, of a compound as described hereinbefore (in a suitable pharmaceutical dosage form), in combined therapy with a progestagen or not.

The androgens according to the invention can also be used in a kit for male contraception. Although this kit can comprise one or more androgens only, it is preferred that it comprises means for the administration of a progestagen and means for the administration of an androgen. The latter means is a pharmaceutical formulation comprising compound according to the invention as described hereinbefore, and a pharmaceutically acceptable carrier.

The invention also pertains to a method of treatment comprising administering to a (notably human) male or female in need of androgen-supplementation a therapeutically effective amount of a (14β,17α)-17-(hydroxymethyl)

steroid as described hereinbefore. This is irrespective of whether or not the need for androgen-supplementation has arisen as a result of male contraception involving the administration of a sterilitant, such as a progestagen.

Further, the invention pertains to a method of contraception, comprising administering to a fertile male, notably human, a (14β,17α)-17-(hydroxymethyl) steroid as described hereinbefore in a dosage amount and regimen which is sufficient for said compound to be contraceptively effective per se. Alternatively, the method of contraception provided by the present invention comprises administering to a fertile male, notably human, a contraceptively effective combination of a sterilitant, such as a progestagen, and a (14β,17α)-17-(hydroxymethyl) steroid as described hereinbefore.

The compounds of the invention may be produced by various methods known in the art of organic chemistry in general, and especially in the art of the chemistry of steroids (see, for example: Fried, J. et al, *Organic Reactions in Steroid Chemistry*, Volumes I and II, Van Nostrand Reinhold Company, New York, 1972).

A convenient starting material for the preparation of compounds of formula I wherein $R_1$ is oxo; $R_2$, $R_4$, $R_7$, $R_8$ and $R_{13}$ are hydrogen; $R_3$ and $R_5$ are hydrogen or ($C_{1-6}$) alkyl; $R_6$ is methyl; $R_9$, $R_{10}$, $R_{11}$ and $R_{12}$ have the previously given meaning; and the dotted lines indicate a $\Delta^4$ double bond, is for instance a compound of general formula II, wherein $R_3$ and $R_5$ are hydrogen or ($C_{1-6}$) alkyl, whose synthesis is known in literature, or which can be prepared using standard methods [see e.g. U.S. Pat. No. 3,407,217 (1965; $R_3$=H, $R_5$=H), FR *1434172 (1966; $R_3$=CH$_3$, $R_5$=H), DE 2539300 (1976; $R_3$=H, $R_5$=CH$_3$), WO 99/26962 ($R_3$=CH$_3$, $R_5$=CH$_3$)].

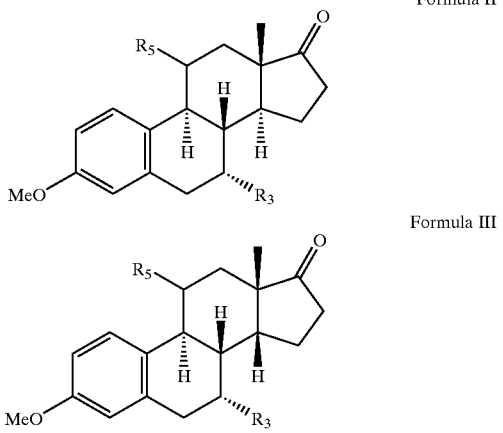

Formula II

Formula III

A possible synthesis route for compounds of the invention starts with the transformation of compounds of formula II into 14β-compounds of formula III using methods described in WO 00/53619. Birch reduction [Caine, D., in Org. Reactions 23, p. 1, Wiley, New York, 1976] and hydrolysis of the resulting (14β,17α)-3-methoxyestra-2,5(10)-dien-17-ol gives a (14β,17α)-17-hydroxyestr-4-en-3-one derivative. The 17-hydroxy group is oxidized (for oxidations, see Hudlicky, M., Oxidations in *Organic Chemistry*, ACS Monograph 186, Washington, D.C., 1990) and the carbonyl group at C-3 is protected, for instance as a cyclic 1,2-ethanediyl dithioacetal.

The resulting (14β)-estr-4-ene-3,17-dione cyclic 3-(1,2-ethanediyl dithioacetal) can be converted to a (14β)-17-[[(trifluoromethyl)sulfonyl]oxy]estra-4,16-dien-3-one cyclic 1,2-ethanediyl dithioacetal derivative by treatment with triflic anhydride and 2,6-di-tert-butyl-4-methylpyridine [Stang, P. J. et al, Synthesis 438 (1979)) or by enolization followed by reaction with N-phenyltrifluoromethanesulfonimide [Mascarenas, J. L. et al, Tetrahedron 47, 3485 (1991)]. The enol triflate can be subjected to a transition metal-catalyzed [Pd, Ni, Pt, etc.] carbonylation in the presence of a alcohol to produce a alkyl (14β)-3,3-[1,2-ethanediylbis(thio)]estra-4,16-diene-17-carboxylate [Cacchi, S. et al, Tetrahedron Lett. 26, 1109 (1985)]. The alkoxycarbonylation can also be carried out starting from a 16-iodoestr-16-ene [Skoda-Földes, R. et al, Tetrahedron 56, 3415 (2000)] or from the corresponding dialkyl phosphonate [Holt, D. A. et al, Tetrahedron Lett. 30, 5393 (1989)].

The alkyl (14β)-3,3-[1,2-ethanediylbis(thio)]estra-4,16-diene-17-carboxylate is reacted with e.g. trimethylsulfoxonium iodide/base [Tarzia, G. et al, Steroids 9, 387 (1967)] to produce a alkyl (14β,16α,17α)-3,3-[1,2-ethanediylbis(thio)]-16,17-dihydro-3'H-cyclopropa[16,17]estra-4,16-diene-17-carboxylate [for cyclopropanation reactions see: Helquist, P., in Comprehensive Organic Synthesis, Vol. 4, p. 951, Pergamon Press, Oxford, N.Y. (1991); Nair, V., ibid., Vol. 4, p. 999 (1991); Larock, R. C., *Comprehensive Organic Transformations*, VCH Publishers, Inc., 1989, p. 71].

Reduction of the ester to the corresponding (14β,16α,17α)-16,17-dihydro-17-(hydroxymethyl)-3'H-cyclopropa[16,17]estra-4,16-dien-3-one cyclic 1,2-ethanediyl dithioacetal derivative and deprotection of the carbonyl group at C-3 then affords a (14β,16α,17α)-16,17-dihydro-17-(hydroxymethyl)-3'H-cyclopropa[16,17]estra-4,16-dien-3-one derivative of the invention.

Optionally, a (14β,16α,17α)-16,17-dihydro-17-(hydroxymethyl)-3'H-cyclopropa[16,17]estra-4,16-dien-3-one cyclic 1,2-ethanediyl dithioacetal derivative can be oxidized to the corresponding 17-carboxaldehyde. The aldehyde can be reacted with an (organometallic) compound of formula $R_{11}M$ in which $R_{11}$ has the previously given meaning except for hydrogen, and M is Li, Na, K, MgX, ZnX, CeX$_2$, SiR$_3$ or SnR$_3$, to produce a 17-(CHR$_{11}$OH) derivative which can be a mixture of C-20 epimers. The latter can be separated whereafter deprotection of the carbonyl group at C-3 provides the 17-(CHR$_{11}$OH) derivatives of the invention in which R., has the previously given meaning except for hydrogen.

Optionally, a (14β,16α,17α)-17-(CHR$_{11}$OH)-16,17-dihydro-3'H-cyclopropa[16,17]estra-4,16-dien-3-one cyclic 1,2-ethanediyl dithioacetal can be oxidized to obtain a 20-ketone which can then be reacted with an (organometallic) compound of formula $R_{12}M$, $R_{12}$ having the previously given meaning except for hydrogen, and M having the previously given meaning. In that case deprotection of the carbonyl group at C-3 will provide 17-(CR$_{11}$R$_{12}$OH) derivatives of the invention wherein $R_{11}$ and $R_{12}$ have the previously given meaning except for hydrogen.

Optionally, the configuration of a 20-hydroxy compound at C-20 can be inverted by oxidation followed by reduction with LiAlH$_4$, NABH$_4$ or other reducing agents. Epimerization at C-20 can also be accomplished by means of a Mitsunobu reaction [Dodge, J. A. et al, Bioorg. & Med. Chem. Left. 6, 1 (1996)], or by treatment with methanesulfonyl chloride or p-toluenesulfonyl chloride followed by reaction with an oxygen nucleophile [e.g. potassium superoxide, see Corey, E. J. et al, Tetrahedron Lett. 3183 (1975)].

Compounds of formula I with substituents at C-3, C-4, C-7, C-10, C-11, C-13, C-15, and C-16 other than those described under the definition of formula II, or compounds with $R_{13}$ other than hydrogen, or compounds without double bonds in the steroid nucleus, or with unsaturations other than a $\Delta^4$ double bond, can be prepared as follows.

Compounds of the invention in which $R_1$ is (H,H), (H,OR), NOR, and R is H, ($C_{1-6}$) alkyl, or ($C_{1-6}$) acyl can be prepared, using standard methods, from compounds of formula I in which $R_1$ is oxo.

Compounds in which $R_2$ is ($C_{1-6}$) alkyl are obtained, using standard methods, from compounds of formula I in which $R_2$ is hydrogen.

Compounds in which $R_3$ has the meaning described above except for hydrogen or ($C_{1-6}$) alkyl can be prepared from e.g. (7α,17β)-7-ethenyl-17-hydroxyestr-4-en-3-one which can be prepared by copper(I)-catalyzed 1,6-addition of vinyllithium or a vinylmagnesium compound to e.g. (17β)-17-(acetyloxy)estra-4,6-diene-3-one [Syntex, DE 1143199 (1963)]. Conversion to (7α)-7-ethenyl-3-methoxyestra-1,3,5(10)-trien-17-one and construction of the functionalized and/or unsaturated side-chain at C-7 from 7-ethenyl are carried out using standard methods. Inversion of the sterebchemistry at C-14, introduction of the 16,17-methylene group and the CH₂OH fragment at C-17 are carried out as described above. The precise sequence of reaction steps needed for these operations is dictated by methods common in synthetic strategy.

Compounds in which $R_4$ is methyl can be prepared from e.g. (3β)-3-(acetyloxy)androsta-5,14-dien-17-one [Andre, A. F. St. et al, J. Am. Chem. Soc. 74, 5506 (1952)].

Compounds in which $R_5$ is ($C_{2-6}$) alkenyl can be obtained from e.g. (11β)-11-(hydroxymethyl)-3-methoxyestra-1,3,5 (10)-trien-17-one cyclic 1,2-ethanediyl acetal [van den Broek, A. J. et al, Steroids 30, 481 (1977)], or 3-methoxyestra-1,3,5(10)-triene-11,17-dione cyclic 17-(1,2-ethanediyl acetal) [van den Broek, A. J. et al, Reel. Trav. Chim. Pays-Bas 9435 (1975)]. Compounds in which $R_6$ is ethyl can be prepared from e.g. 13-ethylgon-4-ene-3,17-dione [Brito, M. et al, Synth. Comm. 26, 623 (1996)].

15-Substituted compounds can be obtained as follows. Conjugated addition of a (organometallic) compound of formula $R_7M$ wherein $R_7$ and M having the previously given meaning, to a (14β)-3-methoxyestra-1,3,5(10),15-tetraen-17-one derivative, prepared from a compound of formula II by methods described in WO 00/53619, provides a (14β)-3-methoxyestra-1,3,5(10)-trien-17-one substituted at C-15, which can then be converted as described above to a 15-substituted compound of the invention.

16-Substituted, compounds can be obtained via alkylation at C-16 of a (14β)-3-methoxyestra-1,3,5(10)-trien-17-one derivative, usually resulting in the predominant formation of the 16β-isomer. Optionally, the stereochemistry at C-16 can be inverted by deprotonation followed by hydrolysis.

Compounds of the invention in which $R_{13}$ is $SO_3H$, or ($C_{1-15}$) acyl are obtained, by using methods known in the art, from compounds of formula I in which $R_{13}$ is hydrogen.

Compounds of the invention without unsaturations in the steroid nucleus are produced from $\Delta^4$ compounds wherein $R_1$ is oxo.

Compounds of the invention having a $\Delta^{5(10)}$ double bond, or a $\Delta^{4,9}$ diene system are produced from $\Delta^4$ compounds wherein $R_1$ is oxo.

Compounds having a $\Delta^{11}$ double bond can be prepared from e.g. estra-4,11-diene-3,17-dione (Broess, A. I. A. et al, Steroids 57, 514 (1992)].

The invention will be further explained hereinafter with reference to the following Examples.

EXAMPLE 1

(7α,14β,16α,17α)-16,17-Dihydro-17-(hydroxymethyl)-7-methyl-3'H-cyclopropa[16,17]estra-4,16-dien-3-one.

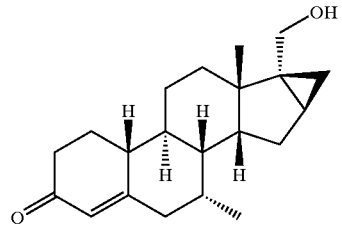

i)—(7α,14β)-3-Methoxy-7-methylestra-1,3,5(10)-trien-17-one [WO 00/53619; 29.24 g] in dry tetrahydrofuran (460 ml) was added to a solution of lithium (41.3 g) in liquid ammonia (1800 ml), cooled to −60 C. After 1 h stirring, tert-butanol (60 ml) and dry tetrahydrofuran (60 ml) were added and stirring was continued for 30 min. Ethanol (765 ml) was added and the ammonia was allowed to evaporate. The mixture was poured into water and the product was extracted into ethyl acetate. The combined organic phases were washed with brine, dried over sodium sulfate and concentrated under reduced pressure, to give (7α,14β,17α)-3-methoxy-7-methylestra-2,5(10)-dien-17-ol (31.23 g). The product was used in the following step without further purification.

ii)—A solution of the diene obtained in the previous step (31.23 g) in acetone (500 ml) was treated with hydrochloric acid (4 M, 50 ml). After 45 min. stirring at room temperature, the reaction mixture was poured into a saturated aqueous solution of sodium hydrogencarbonate. The product was extracted into ethyl acetate; the combined organic phases were washed with brine, dried over sodium sulfate and concentrated under reduced pressure, to give (7α,14β,17α)-17-hydroxy-7-methylestr-4-en-3-one (28.69 g). The product was used in the following step without further purification.

iii)—A solution of the product obtained in the previous step (47.8 g) in acetone (2648 ml) was cooled to 0° C. Jones reagent (8 M, 52.8 ml) was added dropwise while keeping the temperature below 10° C. The reaction mixture was stirred for 10 min. 2-Propanol (45 ml) was added and after 10 min. stirring the mixture was filtered over dicalite. The filtrate was concentrated under reduced pressure and the residue was dissolved into ethyl acetate. The resulting solution was washed with a saturated aqueous solution of sodium hydrogencarbonate and brine, dried over sodium sulfate and concentrated under reduced pressure, to give (7α,14β)-7-methylestr-4-ene-3,17-dione (45.8 g). The product was used in the following step without further purification.

iv)—Boron trifluoride diethyl etherate (9.8 ml) was added to a mixture of the product obtained in the previous step (45.8 g), 1,2-ethanedithiol (13.8 ml), and dry methanol (414 ml), cooled to 0° C. After 2 h stirring while allowing to raise the temperature to 20° C., the reaction mixture was poured into water. The product was extracted into ethyl acetate; the combined organic phases were washed with aqueous sodium hydroxide (10%) and brine, dried over sodium sulfate and concentrated under reduced pressure. Column chromatography gave (7α,14β)-7-methylestr-4-ene-3,17-dione cyclic 31 (1,2-ethanediyl dithioacetal) (47.4 g).

v)—A solution of the product obtained in the previous step (47.48 g) in dry tetrahydrofuran (392 ml) was cooled to 0° C. and treated with lithium bis(trimethylsilyl)amide (1 M solution in tetrahydrofuran, 392 ml). After 30 min. stirring N-phenyltrifluoromethanesulfonimide (141 g) was added and stirring was continued for 30 min. The mixture was poured into water and the product was extracted into ethyl acetate. The combined organic phases were washed with brine, dried over sodium sulfate and concentrated under reduced pressure. Column chromatography gave (7α,14β)-7-methyl-17-[[(trifluoromethyl)sulfonyl]oxy]estra-4,16-dien-3-one cyclic 1,2-ethanediyl dithioacetal (21.49 g).

vi)—A solution of the product obtained in the previous step (11.0 g) in a mixture of dimethyl formamide (160 ml), methanol (49 ml) and triethylamine (8 ml) was degassed with argon and then saturated with carbon monoxide. It was treated with triphenylphosphine (1.02 g) and palladium(II) acetate (0.568 g). While passing CO through the reaction mixture it was stirred for 2 h at room temperature. The mixture was poured into water and the product was extracted into ethyl acetate. The combined organic phases were washed with brine, dried over sodium sulfate and concentrated under reduced pressure. Column chromatography gave methyl (7α,14β)-3,3-[1,2-ethanediylbis(thio)]-7-methylestra-4,16-diene-17-carboxylate (7.08 g).

vii)—Sodium hydride (60% suspension in mineral oil, 5.28 g) was added to a suspension of trimethylsulfoxonium iodide (29.1 g) in dry dimethyl sulfoxide (606 ml) and the mixture was stirred at room temperature for 30 min. A solution of the product obtained in the previous step (13.7 g) in dry tetrahydrofuran (70 ml) was added and the reaction mixture was stirred overnight. The mixture was poured into ice-water and the product was extracted into ethyl acetate. The combined organic phases were washed with brine, dried over sodium sulfate and concentrated under reduced pressure, to give methyl (7α,14β,16α,17α)-3,3-[1,2-ethanediylbis(thio)]-16,17-dihydro-7-methyl-3'H-cyclopropa[16;17]estra-4,16-diene-17-carboxylate (15.5 g). The product was used in the following step without further purification.

viii)—A solution of the compound obtained in the previous step (15.0 g) in dry toluene (290 ml) was cooled to −78° C. and treated with diisobutylaluminium hydride (20% solution in toluene, 91.8 ml). The reaction mixture was stirred for 1 h. and quenched with an aqueous solution of acetic acid (10%, 100 ml). The product was extracted into ethyl acetate. The combined organic phases were washed with a saturated aqueous solution of sodium hydrogencarbonate and brine, dried over sodium sulfate and concentrated under reduced pressure, to give (7α,14β,16α,17α)-16,17-dihydro-17-(hydroxymethyl)-7-methyl-3'H-cyclopropa[16,17]estra-4,16-dien-3-one cyclic 1,2-ethanediyl dithioacetal (15.5 g). The product was used in the following step without further purification.

ix)—A solution of the product obtained in the previous step (2.16 g) in a mixture of dichloromethane (11 ml) and methanol (11 ml) was treated with an aqueous solution of periodic acid (0.13 g/ml, 4.44 ml). After 45 min. stirring at room temperature, the reaction mixture was poured into a saturated aqueous solution of sodium hydrogencarbonate and the product was extracted into ethyl acetate. The combined organic phases were washed with a saturated aqueous solution of sodium thiosulfate and brine, dried over sodium sulfate and concentrated under reduced pressure. Column chromatography afforded (7α,14β,16α,17α)-16,17-dihydro-17-(hydroxymethyl)-7-methyl-3'H-cyclopropa[16,17]estra-4,16-dien-3-one (0.67 g). $^1$H NMR (CDCl$_3$) δ 5.80 (t, 1H, J=2.4 Hz), 4.08 (m, 1H), 3.24 (dd, 1H, J=11.8 and 3.5 Hz), 1.15 (s, 3H), 0.81 (d, 3H, J=7.5 Hz), 0.64 (m, 1H), 0.32 (dd, 1H, J=7.9 and 4.7 Hz).

EXAMPLE 2

(7α,14β,16α,17α,20S)-16,17-Dihydro-20-hydroxy-7-methyl-3'H-cyclopropa[16,17]-19-norpregna-4,16-dien-3-one.

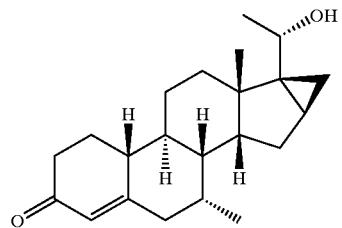

i)—Tetrapropylammonium perruthenate (0.753 g) was added to a solution of (7α,14β,16α,17α)-16,17-dihydro-17-(hydroxymethyl)-7-methyl-3'H-cyclopropa[16,17]estra-4,16-dien-3-one cyclic 1,2-ethanediyl dithioacetal (Example 1, step viii; 13.4 g) and 4-methylmorpholine N-oxide (12.3 g) in acetone (274 ml). After 2 h stirring at room temperature the reaction mixture was filtered over dicalite and silica. The filtrate was concentrated under reduced pressure. Column chromatography of the crude product gave (7α,14β,16α,17α)-17-formyl-16,17-dihydro-7-methyl-3'H-cyclopropa[16,17]estra-4,16-dien-3-one cyclic 3-(1,2-ethanediyl dithioacetal) (5.86 g).

ii)—A solution of the product obtained in the previous step (1.50 g) in dry tetrahydrofuran (5 ml) was added dropwise to methylmagnesium chloride (1.5 M solution in tetrahydrofuran, 25 ml), cooled to 0° C. After 30 min. stirring, the reaction mixture was poured into a saturated aqueous solution of ammonium chloride. The product was extracted into diethyl ether; the combined organic phases were washed with brine, dried over sodium sulfate and concentrated under reduced pressure, to give (7α,14β,16α,17α,20R)-16,17-dihydro-20-hydroxy-7-methyl-3'H-cyclopropa[16,17]-19-norpregna-4,16-dien-3-one cyclic 1,2-ethanediyl dithioacetal (1.59 g). The product was used in the following step without further purification.

iii)—Diethyl azodicarboxylate (1.37 ml) was added dropwise to an ice-cooled solution of the product obtained in the previous step (1.28 g), triphenylphosphine (2.18 g) and p-nitrobenzoic acid (1.39 g) in dry toluene (34.4 ml). The reaction mixture was stirred for 2 h and then poured into brine. The product was extracted into ethyl acetate; the combined organic phases were washed with brine, dried over sodium sulfate and concentrated under reduced pressure. Column chromatography afforded (7α,14β,16α,17α, 20S)-16,17-dihydro-7-methyl-20-[(p-nitrobenzoyl)oxy]-3'H-cyclopropa[16,17]-19-norpregna-4,16-dien-3-one cyclic 1,2-ethanediyl dithioacetal (0.83 g).

iv)—Potassium hydroxide (0.34 g) was added in portions to a solution of the product obtained in the previous step (0.83 g) in tetrahydrofuran (4 ml), methanol (3 ml), and water (1 ml). The reaction mixture was stirred for 3 h at room temperature and then poured into brine. The product was extracted into ethyl acetate; the combined organic phases were washed with brine, dried over sodium sulfate and concentrated under reduced pressure, to give (7α,14β, 16α,17α,20S)-16,17-dihydro-20-hydroxy-7-methyl-3'H-cyclopropa[16,17]-19-norpregna-4,1,6-dien-3-one cyclic 1,2-ethanediyl dithioacetal (0.50 g). The product was used in the following step without further purification.

v)—Following a procedure analogous to that described under ix of Example 1, the product obtained in the previous step (0.20 g) was converted to (7α,14β,16α,17α,20S)-16, 17-dihydro-20-hydroxy-7-methyl-3'H-cyclopropa[16,17]-19-norpregna-4,16-dien-3-one (0.125 g). $^1$H NMR (CDCl$_3$) δ 5.80 (m, 1H), 4.35 (q, 1H, J=6.9 Hz), 1.18 (s, 3H), 0.91 (d, 3H, J=6.7 Hz), 0.81 (d, 3H, J=7.1 Hz), 0.47 (m, 1H), 0.42 (m, 1H).

EXAMPLE 3

In a manner analogous to the procedures described in Example 2, and using (7α,14β,16α,17α)-17-formyl-16,17-dihydro-7-methyl-3'H-cyclopropa[16,17]estra-4, 16-dien-3-one cyclic 3-(1,2-ethanediyl dithioacetal) (Example 2, step i) as starting material, the following products were prepared:
a)—[7α,14β,16α,17α(20S)]-16,17-Dihydro-20-(1-hydroxypropyl)-7-methyl-3'H-cyclopropa [16,17]estra-4, 16-dien-3-one.

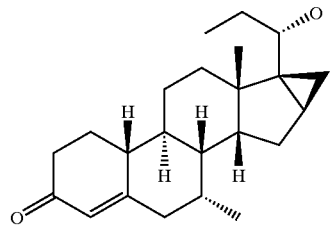

$^1$H NMR (CDCl$_3$) δ 5.80 (m, 1H), 3.92 (q, 1H, J=7.1 Hz), 1.17 (s, 3H), 0.93 (d, 1H, J=7.5 Hz), 0.81 (d, 3H, J=7.1 Hz), 0.49 (m, 1H), 0.35 (dd, 1H, J 8.3 and 5.1 Hz).
b)—[7α,14β,16α,17α(20S)]-16,17-Dihydro-20-(1-hydroxy-2-propynyl)-7-methyl-3 'H-cyclopropa[16,17]estra-4,16-dien-3-one.

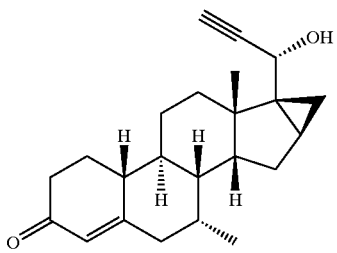

$^1$H NMR (CDCl$_3$) δ 5.80 (m, 1H), 4.99 (dd, 1H, J=8.3 and 2.0 Hz), 2.35 (d, 1H, J 2.0 Hz), 1.18 (s, 3H), 0.81 (d, 3H, J=7.1 Hz), 0.77 (dd, 1H, J=8.3 and 5.1 Hz), 0.61 (m, 1H).

EXAMPLE 4
(3β,7α,14β,16α,17α)-16,17-Dihydro-17-(hydroxymethyl)-7-methyl-3'H-cyclopropa[16,17]estra-4,16-dien-3-ol.

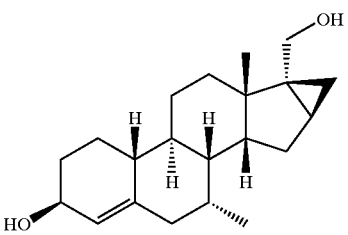

i)—A solution of (7α,14β,16α,17α)-16,17-dihydro-17-(hydroxymethyl)-7-methyl-3'H-cyclopropa[16,17]estra-4,16-dien-3-one (Example 1; 0.074 g) in dry tetrahydrofuran (4 ml), cooled to 0° C., was treated with solid lithium aluminium hydride (0.038 g). After 30 min. stirring, the reaction was quenched by addition of a saturated aqueous solution of sodium sulfate. Ethyl acetate was added, and the mixture was filtered over dicalite. The filtrate was concentrated under reduced pressure to give (3β,7α,14β,16α,17α)-16,17-dihydro-17-(hydroxymethyl)-7-methyl-3'H-cyclopropa[16,17]estra-4,16-dien-3-ol (0.069 g). $^1$H NMR (CDCl$_3$) δ 5.33 (m, 1H), 4.21 (m, 1H), 4.07 (dd, 1H, J=11.8 and 7.5 Hz), 3.22 (dd, 1H, J=11.8 and 3.9 Hz), 1.12 (s, 3H), 0.77 (d, 3H, J=7.1 Hz), 0.63 (tm, 1H, J=3.9 Hz), 0.29 (dd, 1H, J=7.9 and 4.7 Hz).

EXAMPLE 5

(3E,7α,14β,16α,17α)-16,17-Dihydro-3-(hydroxyimino)-7-methyl-3'H-cyclopropa[16,17]estra-4,16-diene-17-methanol (a) and (3Z,7α,14β,16α,17α)-16,17-dihydro-3-(hydroxyimino)-7-methyl-3'H-cyclopropa[16,17]estra-4,16-diene-17-methanol (b).

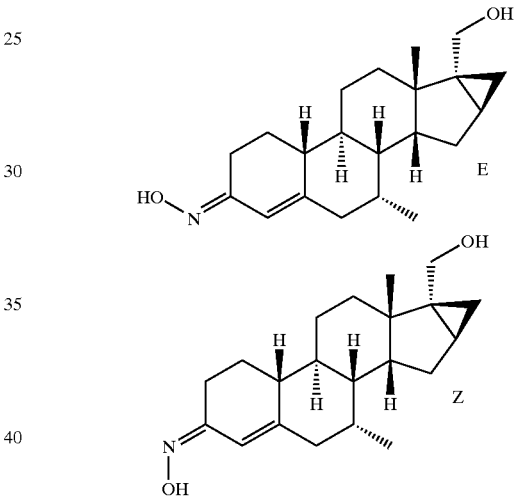

To a solution of (7α,14β,16α,17α)-16,17-dihydro-17-(hydroxymethyl)-7-methyl-3'H-cyclopropa[16,17]estra-4,16-dien-3-one (Example 1; 0.041 g) in pyridine (0.5 ml) was added hydroxylamine hydrochloride (0.122 g). The reaction mixture was stirred at reflux temperature for 45 min. After cooling, the mixture was poured into water. The product was extracted into diethyl ether; the combined organic phases were washed with brine, dried over sodium sulfate and concentrated under reduced pressure. Column chromatography afforded (3E,7α,14β,16α,17α)-16,17-dihydro-3-(hydroxyimino)-7-methyl-3'H-cyclopropa[16,17]estra-4, 16-diene-17-methanol (0.0125 g), $^1$H NMR (CDCl$_3$) δ 5.81 (m, 1H), 4.08 (d, 1H, J=11.8 Hz), 3.23 (d, 1H, J=11.8 Hz), 3.12 (dt, 1H, J=16.5 and 3.9 Hz), 1.15 (s, 3H), 0.79 (d, 3H, J=7.1 Hz), 0.64 (t, 1H, J=4.3 Hz), 0.30 (dd, 1H, J=7.9 and 5.1. Hz); and (3Z,7α,14β,16α,17α)-16,17-dihydro-3-(hydroxyimino)-7-methyl-3'H-cyclopropa[16,17]estra-4, 16-diene-17-methanol (0.0146 g), $^1$H NMR (CDCl$_3$) δ 6.50 (m, 1H), 4.08 (d, 1H, J=11.8 Hz), 3.23 (d, 1H, J=11.8 Hz), 1.14 (s, 3H), 0.80 (d, 3H, J=7.1 Hz), 0.63 (tm, 1H, J=3.9 Hz), 0.31 (dd, 1H, J=7.9 and 5.1 Hz).

EXAMPLE 6

(14β,16α,17α)-16,17-Dihydro-17-(hydroxymethyl)-3'H-cyclopropa[16,17]estra-4,16-dien-3-one.

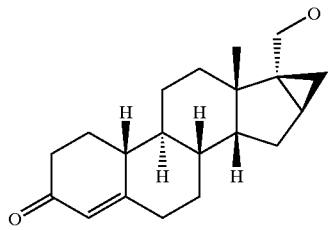

The title compound was prepared from (14β)-3-methoxyestra-1,3,5(10)-trien-17-one [Johnson, W. S. et al, J. Am. Chem. Soc. 79, 2005 (1957)] using procedures analogous to those described under Example 1. $^1$H NMR (CDCl$_3$) δ 5.81 (bs, 1H), 4.10 (ddd, 1H, J=11.4, 7.9 and 0.8 Hz), 3.23 (dd, 1H, J=11.4 and 3.9 Hz), 1.15 (s, 3H), 0.64 (m, 1H), 0.34 (dd, 1H, J=7.9 and 5.1 Hz).

EXAMPLE 7

(5α,14β,16α,17α)-16,17-Dihydro-17-(hydroxymethyl)-3'H-cyclopropa[16,17]estr-16-en-3-one.

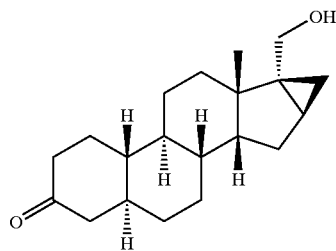

A refluxing solution of (14β,16α,17α)-16,17-dihydro-17-(hydroxymethyl)-3'H-cyclopropa[16,17]estra-4,16-dien-3-one (Example 6; 0.050 g) in a mixture of liquid ammonia (10 ml) and dry tetrahydrofuran (3.0 ml) was treated with granular lithium until the blue colour did not disappear anymore. The reaction mixture was stirred for 30 min. and then quenched with solid ammonium chloride. The ammonia was allowed to evaporate, water was added, and the product was extracted into ethyl acetate. The combined organic phases were washed with a saturated aqueous solution of ammonium chloride and brine, dried over sodium sulfate and concentrated under reduced pressure. Column chromatography afforded (5α,14β,16α,17α)-16,17-dihydro-17-(hydroxymethyl)-3'H-cyclopropa[16,17]estr-16-en-3-one (0.022 g). $^1$H NMR (CDCl$_3$) δ 4.09 (dd, 1H, J=11.5 and 7.1 Hz), 3.22 (dd, 1H, J=11.9 and 3.6 Hz), 1.12 (s, 3H), 0.63 (m, 1H), 0.32 (dd, 1H, J=7.9 and 4.7 Hz).

EXAMPLE 8

Biological Results

The compounds according to the invention were tested for androgenic activity (the procedures for which have been described above) and rated according to the following scheme:

| Example | Result |
| --- | --- |
| 1 | +++ |
| 2 | ++ |
| 3a | ++ |
| 3b | ++ |
| 4 | (prodrug) |
| 5a | (prodrug) |
| 5b | (prodrug) |
| 6 | ++ |
| 7 | ++ |

(+) androgenic activity found;
(++) high androgenic activity;
(+++) excellent androgenic activity.

EXAMPLE 9

Comparative Example

The transactivative androgen activity was determined in a comparison of the following compounds: the compound of Example 1 according to the invention, i.e. (7α,14β,16α,17α)-16,17-dihydro-17-(hydroxymethyl)-7-methyl-3'H-cyclopropa[16,17]estra-4,16-dien-3-one, and compounds denoted C1 and C2, not according to the invention, which respectively are (7α,14β,16β,17α)-17-(hydroxymethyl)-7,16-dimethylestr-4-en-3-one and (7α,14β,17α)-17-(hydroxymethyl)-7,17-dimethylestr-4-en-3-one as disclosed in WO 00/53619. The results are given below:

| Example | Transactivative androgen activity |
| --- | --- |
| 1 | 263 |
| C1 | 72 |
| C2 | 22 |

We claim:

1. A (14β,17α)-7-(hydroxymethyl) steroid, wherein it carries a β-oriented, annellated cyclopropyl group which includes carbon atoms 16 and 17 of the steroid skeleton.

2. The (14β,17α)-17-(hydroxymethyl) steroid according to claim 1, wherein it satisfies structural formula I:

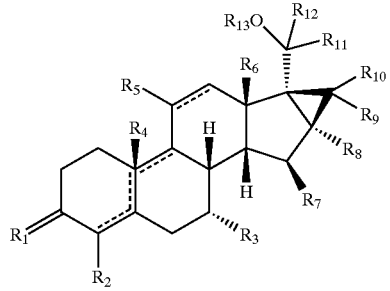

Formula I wherein
R$_1$ is O, (H,H), (H,OR), NOR, with R being hydrogen, (C$_{1-6}$)alkyl, (C$_{1-6}$) acyl;
R$_2$ is hydrogen, or (C$_{1-6}$)alkyl;
R$_3$ is hydrogen; or R$_3$ is (C$_{1-6}$)alkyl, (C$_{2-6}$)alkenyl, or (C$_{2-6}$)alkynyl, optionally substituted by halogen;
R$_4$ is hydrogen, or (C$_{1-6}$)alkyl;
R$_5$ is hydrogen, (C$_{1-6}$)alkyl, or (C$_{2-6}$)alkenyl;
R$_6$ is (C$_{1-6}$)alkyl;
R$_1$ is hydrogen, (C$_{1-6}$)alkyl or (C$_{2-6}$)alkenyl, or (C$_{1-6}$) alkoxy;

$R_8$ is hydrogen, or $(C_{1-6})$alkyl;

$R_9$ and $R_{10}$ are independently hydrogen, $(C_{1-4})$alkoxy, halogen, $(C_{1-4})$alkyl, or $(C_{2-4})$alkenyl;

$R_{11}$ and $R_{12}$ are independently hydrogen, $(C_{1-6})$ alkyl, $(C_{2-6})$alkenyl, $(C_{3-6})$cycloalkyl, $(C_{5-6})$cycloalkenyl, or $(C_{2-6})$alkynyl, each optionally substituted by $(C_{1-4})$ alkoxy, or halogen;

$R_{13}$ is hydrogen, $SO_3H$, or $(C_{1-15})$acyl; and the dotted lines indicate optional bonds.

3. A The steroid according to claim 2, wherein $R_4$ is hydrogen; $R_6$ is methyl and; there is neither a $\Delta^{5(10)}$ nor a $\Delta^{11(12)}$ double bond.

4. A The steroid according to claim 3, wherein $R_1$ is O, (H,H), (H,OH);

$R_2$ is hydrogen, or methyl;

$R_3$ is hydrogen, methyl, ethyl or vinyl;

$R_5$ is hydrogen or methyl;

$R_7$ is hydrogen;

$R_8$ is hydrogen;

$R_9$ is hydrogen, $(C_{1-4})$alkoxy, halogen, $(C_{1-4})$alkyl, or $(C_{2-4})$ alkenyl;

$R_{10}$ is hydrogen;

$R_{11}$ and $R_{12}$ are independently hydrogen, $(C_{1-6})$ alkyl, $(C_{2-6})$alkenyl, $(C_{3-6})$cycloalkyl, $(C_{5-6})$cycloalkenyl, or $(C_{2-6})$alkynyl each optionally substituted by $(C_{1-4})$ alkoxy, or halogen.

5. A The steroid according to claim 4, wherein one of $R_{11}$ and $R_{12}$ is hydrogen and the other is hydrogen or 20S methyl, 20S ethyl or 20S ethynyl.

6. A The steroid according to claim 5, wherein $R_2$ is hydrogen;

$R_5$ is hydrogen;

$R_9$ is hydrogen;

$R_{11}$ and $R_{12}$ are (H,20S methyl) and the steroid does not have a $\Delta^{9(10)}$ double bond.

7. A The steroid according to claim 2, wherein $R_3$ is hydrogen or methyl.

8. A The steroid according to claim 2, wherein $R_{13}$ is hydrogen or acyl; $R_1$ is O or (H,$\beta$OH) and the compound has a $\Delta^{4(5)}$ double bond.

9. The steroid according to claim 8, wherein it is (7α,14β,16α,17α)-16,17-dihydro-17-(hydroxymethyl)-7-methyl-3'H-cyclopropa[16,17]estra-4,16-dien-3-one or (3β,7α,14β,16α,17α)-16,17-dihydro-17-(hydroxymethyl)-7-methyl-3'H-cyclopropa[16,17]estra-4,16-dien-3-ol.

10. A pharmaceutical composition, comprising:

the (14β,17α)-17-(hydroxymethyl) steroid according to claim 1, and a pharmaceutically acceptable carrier.

11. A kit for male contraception, comprising:

a means for administering a progestagen and a means for administering an androgen, wherein the androgen is a (14β,17α)-17-(hydroxymethyl) steroid according to claim 1.

12. A method of treating androgen-deficiency, comprising:

administering to a patient suffering from androgen-deficiency an effective amount of the (14β,17α)-17-(hydroxymethyl) steroid according to claim 1.

13. A method of contraception, comprising, administering to a male patient an effective amount of the (14β,17α)-17-(hydroxymethyl) steroid according to claim 1.

* * * * *

UNITED STATES PATENT AND TRADEMARK OFFICE
CERTIFICATE OF CORRECTION

| | | |
|---|---|---|
| PATENT NO. | : 6,949,531 B2 | |
| APPLICATION NO. | : 10/450278 | |
| DATED | : September 27, 2005 | |
| INVENTOR(S) | : Jaap Van Der Louw | |

It is certified that error appears in the above-identified patent and that said Letters Patent is hereby corrected as shown below:

Claim 1, Col. 14, line 37:

A (14β, 17α)-7-(hydroxymethyl) steroid, wherein it should read

A (14β, 17α)-17-(hydroxymethyl) steroid, wherein it

Claim 2, Col. 14, line 66:

$R_1$ is hydrogen, $(C_{1-6})$alkyl or $(C_{2-6})$alkenyl, or $(C_{1-6})$ should read

$R_7$ is hydrogen, $(C_{1-6})$alkyl or $(C_{2-6})$alkenyl, or $(C_{1-6})$

Signed and Sealed this

Eighteenth Day of September, 2007

JON W. DUDAS
*Director of the United States Patent and Trademark Office*